(12) United States Patent
Roth et al.

(10) Patent No.: US 8,812,097 B2
(45) Date of Patent: Aug. 19, 2014

(54) NEUROLOGICALLY BASED NON-INVASIVE BLOOD GLUCOSE CONCENTRATION SYSTEM AND METHOD

(75) Inventors: Hans Roth, Phoenix, AZ (US); Santosh Mathan, Seattle, WA (US)

(73) Assignee: Honeywell International Inc., Morristown, NJ (US)

( * ) Notice: Subject to any disclaimer, the term of this patent is extended or adjusted under 35 U.S.C. 154(b) by 327 days.

(21) Appl. No.: 13/366,698

(22) Filed: Feb. 6, 2012

(65) Prior Publication Data

US 2013/0204152 A1 Aug. 8, 2013

(51) Int. Cl.
*A61B 5/0484* (2006.01)

(52) U.S. Cl.
USPC .......................................... 600/544; 600/319

(58) Field of Classification Search
CPC ............. A61B 5/14532; A61B 5/6821; A61B 5/0476; A61B 5/04012; A61B 5/04001; A61B 5/0484
USPC .................... 600/319, 365, 544, 545
See application file for complete search history.

(56) References Cited

U.S. PATENT DOCUMENTS

| 5,713,353 | A | 2/1998 | Castano |
|---|---|---|---|
| 6,572,542 | B1 | 6/2003 | Houben et al. |
| 6,704,588 | B2 | 3/2004 | Ansari et al. |
| 6,889,069 | B2 | 5/2005 | Routt et al. |
| 6,895,264 | B2 | 5/2005 | Rice et al. |
| 2004/0087843 | A1 | 5/2004 | Rice et al. |
| 2004/0147820 | A1 | 7/2004 | Routt et al. |
| 2006/0020184 | A1 | 1/2006 | Woods et al. |
| 2006/0183986 | A1 | 8/2006 | Rice et al. |
| 2006/0200013 | A1 | 9/2006 | Smith et al. |
| 2008/0255438 | A1* | 10/2008 | Saidara et al. ................ 600/365 |
| 2009/0287107 | A1 | 11/2009 | Beck-Nielsen et al. |
| 2010/0036453 | A1 | 2/2010 | Hulvershorn et al. |
| 2010/0238404 | A1 | 9/2010 | Newman et al. |

FOREIGN PATENT DOCUMENTS

| WO | 2004112601 A1 | 12/2004 |
|---|---|---|
| WO | 2006029097 A2 | 3/2006 |

OTHER PUBLICATIONS

Elisabeth Rungger-Brdndle, Helga Kolb, Gunter Niemey, "Histochemical Demonstration of Glycogen in Neurons of the Cat Retina", Investigative Ophthalmology & Visual Science, Apr. 1996, vol. 37, No. 5.

Claudio Macaluso, Shoken Onoe, Gunter Niemeyer, "Changes in Glucose Level Affect Rod Function More Than Cone Function in the Isolated, Perfused Cat Eye", Investigative Ophthalmology & Visual Science, vol. 33, No. 10, Sep. 1992.

Leslie C. Macgregor, Franz M. Matschinsky, "Altered Retinal Metabolism in Diabetes-Measurement of Sodium-Potassium ATPase and Total Sodium and Potassium in Individual Retinal Layers", The Journal of Biological Chemistry, vol. 261, No. 9, Issue of Mar. 25, pp. 4052-4058, 1986.

(Continued)

*Primary Examiner* — Navin Natnithithadha
*Assistant Examiner* — Etsub Berhanu
(74) *Attorney, Agent, or Firm* — Ingrassia Fisher & Lorenz, P.C.

(57) ABSTRACT

A non-invasive blood glucose concentration sensing system and method includes sensing neurophysiological brain activity of the user during visual pigment regeneration in an eye of the user, and correlating the sensed neurophysiological brain activity to the glucose concentration in the blood of the user.

17 Claims, 3 Drawing Sheets

(56) References Cited

OTHER PUBLICATIONS

Dan Zhang, Yijun Wang, Alexander Maye, Andreas K. Engel, Xiaorong Gao, Bo Hong, and Shangkai Gao, "A Brain-Computer Interface Based on Multi-Modal Attention", Proceedings of the 3rd International IEEE EMBS Conference on Neural Engineering, Kohala Coast, Hawaii, USA, May 2-5, 2007, FrD3.24.

David J. Ramsey, Harris Ripps, Haohua Qian, "An Electrophysiological Study of Retinal Function in the Diabetic Female Rat", Investigative Ophthalmology & Visual Science, Nov. 2006, vol. 47, No. 11.

GB Combined Search and Examination Report for Application No. GB1301823.9 dated May 1, 2013.

* cited by examiner

NEUROLOGICALLY BASED NON-INVASIVE BLOOD GLUCOSE CONCENTRATION SYSTEM AND METHOD

TECHNICAL FIELD

The present invention generally relates to blood glucose concentration measurement, and more particularly to a neurologically based non-invasive blood glucose concentration system and method.

BACKGROUND

It is estimated that by the year 2016, upwards of sixteen billion dollars ($16B) will be spent annually on blood glucose diagnostics and testing. This may be an inaccurately low estimate since many diabetics (and potential diabetics), for various reasons, are unwilling to test themselves. One of the most prevalent reasons has to do with the self-testing methodologies, which have advanced relatively little over the past 30 years. Most methodologies continue to rely on arcane finger pricking that can cause pain, discomfort, and inconvenience for users.

In recent years, efforts have been made to implement and bring to market various types of sufficiently accurate, non-invasive blood glucose concentration testing methods. Some of these methods include passing light waves through solid tissues, such as a fingertip or an ear lobe, and measuring the molecular absorption spectrum of glucose. Because of the variability of absorption and scatter of electromagnetic energy in solid tissue, these methods have been generally unsuccessful. Other methods include measuring blood glucose in various other body fluids, such as the anterior chamber, tears, and interstitial fluids. These methods have shown only limited success.

Another method that was once thought promising, centers around the discovery that the regeneration rate of visual pigment in the eyes depends strongly on the blood glucose concentration, and that visual pigment regeneration could be measured within seconds of bleaching the visual pigment in the retina of an eye. This methodology has thus far proved commercially unsuccessful due to its inability to measure subtle changes in blood glucose concentration from direct measurement of pigment regeneration.

Hence, there is a need for a relatively simple, painless, non-invasive system and method for determining a person's blood glucose concentration. The present invention addresses at least this need.

BRIEF SUMMARY

In one embodiment a method for determining glucose concentration in the blood of a user includes sensing neurophysiological brain activity of the user during visual pigment regeneration in an eye of the user, and correlating the sensed neurophysiological brain activity to the glucose concentration in the blood of the user.

In another embodiment, a method for determining glucose concentration in the blood of a user includes bleaching retinal pigments in the eye of the user to cause the eye to undergo retinal pigment regeneration, presenting a visual perceptual task to the user during the retinal pigment regeneration, sensing neurophysiological brain activity of the user while presenting the visual perceptual task. And correlating the sensed neurophysiological brain activity to the glucose concentration in the blood of the user.

In yet another embodiment, a non-invasive blood glucose concentration sensing system includes a neurophysiological brain activity sensor and a processor. The neurophysiological brain activity sensor is configured to sense neurophysiological brain activity of a user and supply neurophysiological brain activity signals representative thereof. The processor is coupled to receive the neurophysiological brain activity signals and is configured, upon receipt thereof, to correlate the sensed neurophysiological brain activity to blood glucose concentration of the user.

Furthermore, other desirable features and characteristics of the systems and methods described herein will become apparent from the subsequent detailed description and the appended claims, taken in conjunction with the accompanying drawings and the preceding background.

BRIEF DESCRIPTION OF THE DRAWINGS

The present invention will hereinafter be described in conjunction with the following drawing figures, wherein like numerals denote like elements, and wherein.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

Figure 1:
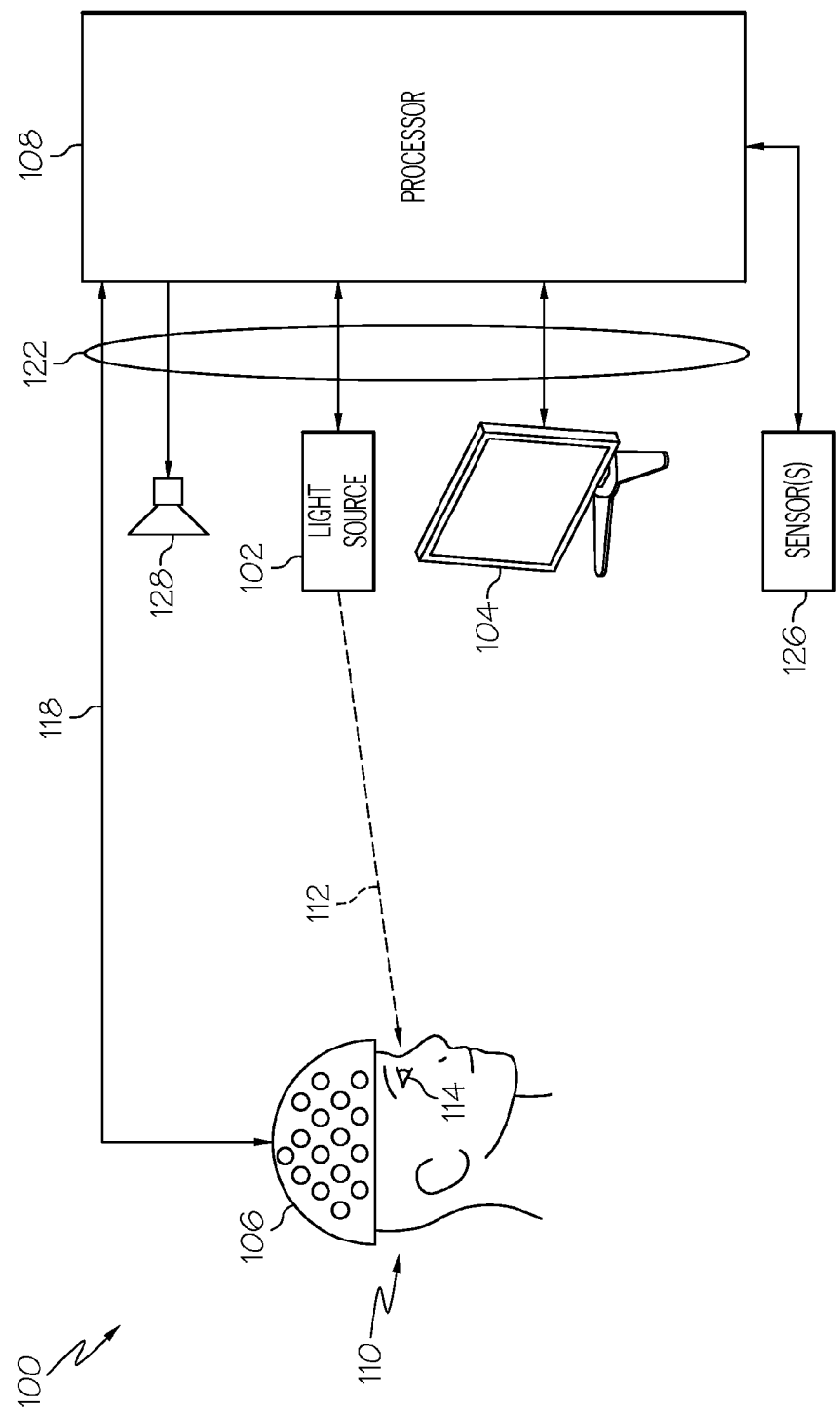
FIG. 1 a functional block diagram of a non-invasive blood glucose concentration sensing system.

Referring to FIG. 1, a functional block diagram of a non-invasive blood glucose concentration sensing system 100 is depicted and includes a light source 102, a display device 104, a neurophysiological brain activity sensor 106, and a processor 108. The light source 102 is in operable communication with the processor 108 and is configured to selectively emit a bleaching light 112 into at least one eye 114 of a user 110. Although the light source 102 is depicted as emitting bleaching light 112 into only one eye 114, it will be appreciated that it could be configured to emit bleaching light 112 into both eyes 114. The bleaching light 112, when emitted into the eye(s) 114 of the user 110, bleaches the retinal pigments in the eye(s) 114. The bleaching of retinal pigments refers to illumination of the rods and cones of a retina by light energy that is capable of breaking down the retinal pigments, and thereby initiating visual pigment regeneration. The configuration and implementation of the light source 102 may vary, and may be any light source that emits light capable of bleaching retinal pigments, including rod and/or cone pigments. Some non-limiting examples of embodiments of the light source 102 include a head-mounted lamp, a glasses-mounted lamp, a chin support with a lamp, an automotive light, a flashlight, a lamp/bleaching device add-on to a mobile device, a camera flash on a stand-alone camera or mobile phone, just to name a few.

The display device 104 is in operable communication with the processor 108 and is configured, in response to display commands received therefrom, to render one or more images. It will be appreciated that the display device 104 may be implemented using any one of numerous known display devices suitable for rendering various types of visual stimuli in a format viewable by the operator 110. Some non-limiting examples of such display devices include various cathode ray tube (CRT) displays, and various flat panel displays such as various types of LCD (liquid crystal display) and TFT (thin film transistor) displays. The display device 108 may additionally be implemented as a panel mounted display, a HUD (head-up display) projection, various portable and/or hand-held displays, or any one of numerous other known technologies.

The neurophysiological brain activity sensor 106 is configured to sense neurophysiological brain activity of the user 110, and to supply neurophysiological brain activity signals 118 representative thereof. In the embodiment depicted in FIG. 1, the neurophysiological brain activity sensor 106 is configured to be disposed on, or otherwise coupled to, the user 110, and is implemented using a plurality of electroencephalogram (EEG) sensors 106. The EEG sensors 106 are configured to be disposed on or near the head of the user 110 by, for example, embedding the EEG sensors 106 in a helmet or cap. The neurophysiological brain activity sensor 106 may additionally be configured to sense various types of neurophysiological brain activity, and thus supply various types of neurophysiological brain activity signals 118. For example, the neurophysiological brain activity sensor 106 may be configured to sense, and supply signals representative of, event related potentials (ERPs) or steady state visual evoked response potentials (SSVEPs). Before proceeding further, a brief discussion of each of these brain activity measures will be provided.

Figure 2:
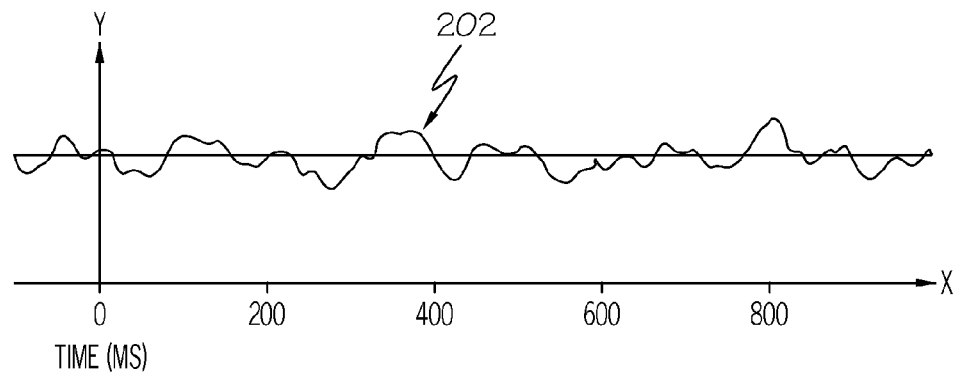
FIG. 2 depicts an exemplary electroencephalogram (EEG) signal supplied from a single EEG electrode in response to a task-irrelevant stimulus.
Figure 3:
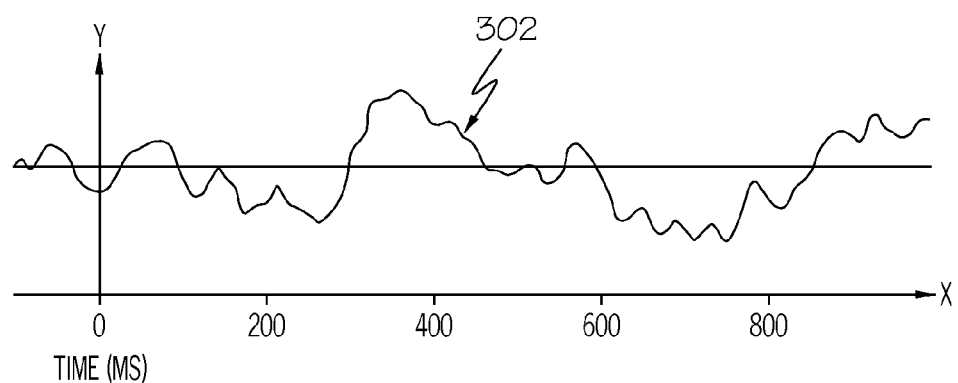
FIG. 3 depicts an exemplary EEG signal supplied from the single EEG electrode in response to a task-relevant stimulus.

An ERP refers to a morphological change in an EEG waveform in response to a task-relevant stimulus, and typically occurs within several hundred milliseconds of the task-relevant stimulus. As an example, FIG. 2 depicts an exemplary EEG signal 202 supplied from a single EEG sensor in response to a task-irrelevant stimulus (e.g., a "distractor"), and FIG. 3 depicts an exemplary EEG signal 302 supplied from the same EEG sensor in response to a task-relevant stimulus (e.g., a "target"). The x-axis in both FIGS. 2 and 3 depicts the progression of time, in milliseconds, following the onset of a stimulus, which occurs at the time-zero point. As may be readily seen, the EEG signal 302 following the task-relevant stimulus exhibits a pronounced amplitude perturbation within a few hundred milliseconds of stimulus onset. It is noted that a task-relevant stimulus may be, for example, displaying an image with a target (e.g., a specific letter, number, object, etc.), and a task-irrelevant image may be, for example, displaying an image without a target.

Figure 4:
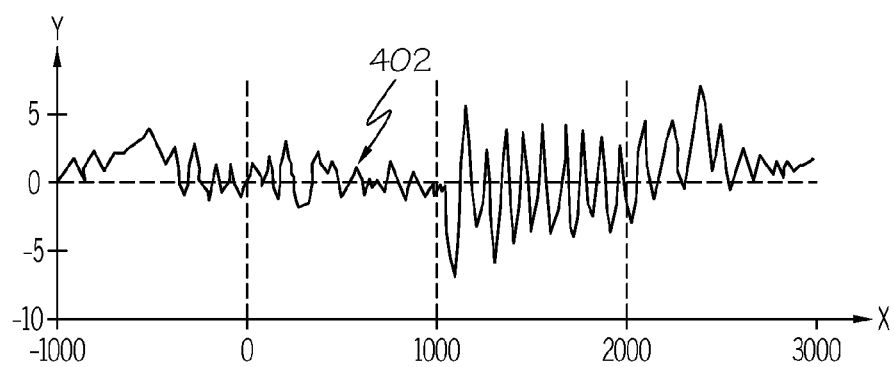
FIG. 4 depicts an exemplary EEG signal supplied from a single EEG electrode in response to an oscillating visual stimulus.

An SSVEP is a harmonic neural response to an oscillating visual stimulus. For example, when a user 110 views a stimulus of a particular frequency, a cluster of neurons in the visual areas of the user's brain (at the back of the head) fire synchronously at the same frequency, and generate a neural signal that is generally referred to as a steady state visual evoked response potential (SSVEP). Thus, as depicted in FIG. 4, when the user 110 views a light or image flashing at 10 Hz, this cluster of neurons fires synchronously at 10 Hz, and an EEG signal 402 supplied from a single EEG sensor oscillates at the 10 Hz, too. The SSVEP signal is robust, consistent across individuals, and can be detected by a relatively small number of EEG sensors.

Returning to FIG. 1, and to the remaining description of the system 100, it is seen that the processor 108 is in operable communication with the light source 102, the display device 104, and the neurophysiological brain activity sensor 106 via, for example, one or more communication buses or cables 122. The processor 108 is coupled to receive the neurophysiological brain activity signals 118 from the neurophysiological brain activity sensor 106. As will be explained momentarily, the processor 108 is configured, upon receipt of the neurophysiological brain activity signals 118, to correlate the sensed neurophysiological brain activity to the blood glucose concentration of the user 110. As will also be explained momentarily, the processor 108 is additionally configured to control the emission of the bleaching light 112 from the light source 102, and to selectively command the display device 104 to present one or more visual perceptual tasks to the user 110.

The processor 108 may be variously implemented, and may include one or more microprocessors, each of which may be any one of numerous known general-purpose microprocessors or application specific processors that operate in response to program instructions. It will additionally be appreciated that the processor 108 may be implemented using various other circuits, not just one or more programmable processors. For example, digital logic circuits and analog signal processing circuits could also be used.

Before proceeding further, it is noted that, at least in some instances, the system 100 may additionally be configured to compensate (e.g., "auto-calibrate") for physiological variables associated with the user 110. To do so, the processor 108 is configured to implement a training routine, during which one or more visual perceptual training tasks are presented to the user 110. Prior to implementing the training routine, the user may be prompted to enter various discrete parameters that may impact the brain-activity-to-blood-glucose-concentration correlation. Such parameters may vary, and may include, for example, their age, their weight, their height, and the time of day, just to name a few. During the training routine, the user 110, via the neurophysiological brain activity sensor 106, supplies initial neurophysiological brain activity signals to the processor 108, thereby establishing baseline neurophysiological brain activity for the user 110.

After the initial training routine, the baseline neurophysiological brain activity, together with additional neurophysiological brain activity that is collected from the user 110 over time, may be used to improve the accuracy of the brain-activity-to-blood-glucose-concentration correlation. Further improvements in the correlation may be realized by including one or more external sensors 126 in the system 100. The one or more sensors 126 may be variously implemented, but are each configured to sense an environmental parameter that, for a given blood glucose concentration, may impact visual pigment regeneration rate. For example, the intensity of, and time of exposure to, light may be sensed via a photodiode (or equivalent sensor) in, for example, a smart phone or other device. The processor 108 may then use the baseline neurophysiological brain activity, the one or more sensed environmental parameters, and the real-time neurophysiological brain activity signals to improve the accuracy of the brain-activity-to-blood-glucose-concentration correlation.

Figure 5:
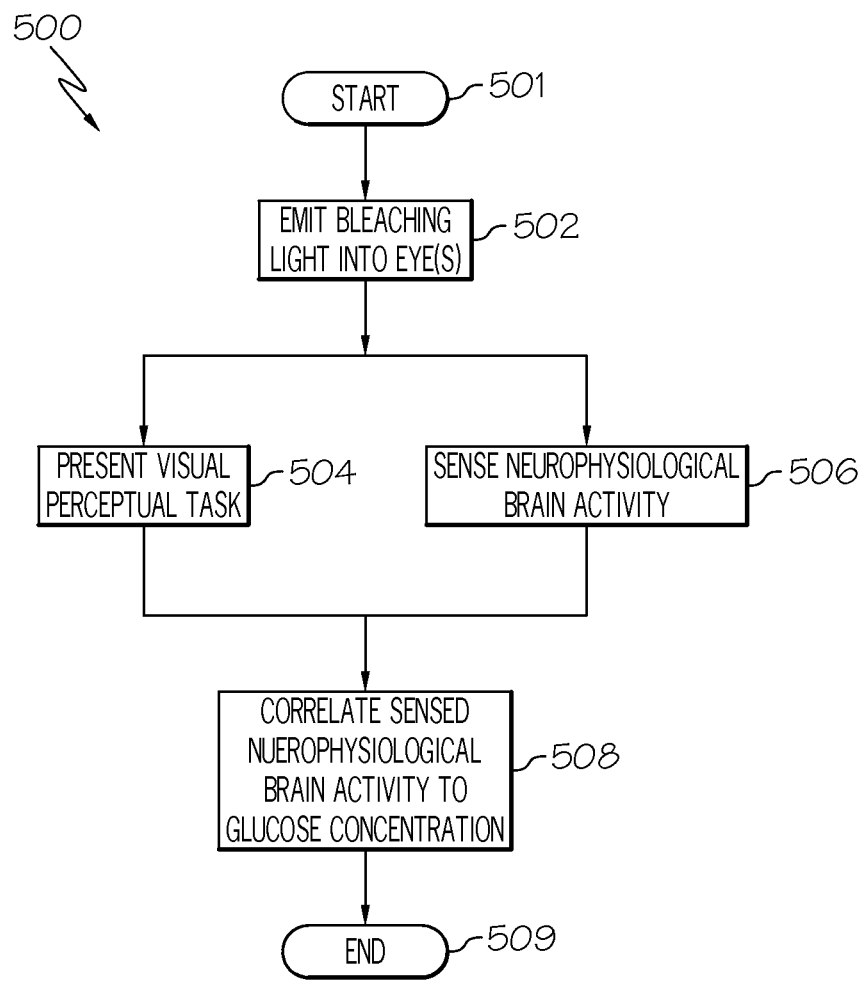
FIG. 5 depicts a process, in flowchart form, that the system of FIG. 1 may implement to determine the blood glucose concentration of a user.

Turning now to FIG. 5, it was noted above that the processor 108, upon receipt of the neurophysiological brain activity signals 118, correlates the sensed neurophysiological brain activity to the blood glucose concentration of the user 110. The processor 108 also controls the emission of the bleaching light 112 from the light source 102, and selectively commands the display device 104 to present one or more visual perceptual tasks to the user 110. The overall process 500 by which the processor 108 implements these functions is depicted in flowchart form in FIG. 5, and will now be described in more detail. Before doing so, however, it is noted that the depicted process 500 is merely exemplary of any one of numerous ways of depicting and implementing the overall process to be described. Moreover, before the process 500 is initiated, it is noted that the neurophysiological brain activity sensor 106 has preferably been properly applied to, and appropriately configured to collect neurophysiological brain activity from, the user 110. It is further noted that the system 100 has been trained using the above-described training routine. With this background in mind, it is additionally noted that the numerical parenthetical references in the following description refer to like blocks in the flowchart depicted in FIG. 5.

Turning now to the description of the process 500, the processor 108 commands the light source 102 to momentarily emit bleaching light 112 into the eye(s) 114 of the user 110 (502). The bleaching light 112, as noted above, bleaches the retinal pigments in the eye(s) 114, causing the eye(s) 114 to undergo retinal pigment regeneration. During the retinal pigment regeneration process, the processor 108 commands the display device 104 to present a visual perceptual task to the user 110 (504), and processes the neurophysiological brain activity signals 118 supplied from the neurophysiological brain activity sensors 106 (506). The processor 108 correlates the sensed neurophysiological brain activity to the glucose concentration in the blood of the user 110 (508). More specifically, the processor 108 correlates the sensed neurological brain activity to the post-bleaching regeneration rate of the visual pigment. As noted above, visual pigment regeneration rate correlates to blood glucose concentration. It should be noted that specific thresholds associated with various blood glucose concentration levels of interest to a user may be determined via empirical tests.

It should be noted that the particular visual perceptual task that the processor 108 commands the display device 104 to present, and the particular neurophysiological brain activity signal processing that the processor 108 implements will vary depending upon the particular brain activity measurement paradigm that is employed. That is, whether the system 100 is configured to implement ERPs or SSVEPs to measure brain activity.

If the system 100 is configured to implement ERPs, then the processor 108 will command the display device 104 to display a plurality of image sequences that are rendered on the display device 104 in brief bursts lasting a few seconds. Each image sequence will include a specific target (e.g., a specific letter, number, object, etc.), which the user 110 is instructed to detect. The processor 108 processes the neurophysiological brain activity signals 118 while the plurality of image sequences are displayed to measure changes in the amplitude and latency of specific peaks in the EEG signals. The processor 108 correlates the changes in amplitude and latency to the visual pigment regeneration rate, and thus to blood glucose concentration.

If the system 100 is configured to implement SSVEPs, then the processor 108 will command the display device 104 to display an image that is oscillating at a predetermined frequency. The processor 108 processes the neurophysiological brain activity signals 118 while the oscillating image is displayed to determine changes in amplitude of the SSVEPs at the predetermined frequency, and correlate the amplitude changes to visual pigment regeneration rate, and thus to blood glucose concentration.

The particular visual perceptual task that the processor 108 commands the display device 104 to present may also vary based on adaptive psychophysical methods. More specifically, the processor 108 may be configured to implement generally known psychophysical techniques to identify a visual perceptual task of a complexity level that is optimal for the user 110. Thus, the visual perceptual task will be neither too easy, nor too difficult.

The system 100 may also be configured to generate one or more alerts and/or to generate various types of feedback. The alerts, which may be implemented audibly, visually, or both, may be used to remind the user 110 to check their blood glucose concentration. The alerts may be rendered on the display device 104, supplied via an audio device 128, or transmitted to a remote device as an email or a text message. The feedback may also be implemented audibly, visually, or both, and is representative of the glucose concentration in the blood of the user. Similar to the alerts, the feedback may be rendered on the display device 104, supplied via an audio device 128, or transmitted to a remote device as an email or a text message.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal In the alternative, the processor and the storage medium may reside as discrete components in a user terminal, or in a cloud-based computing platform.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. The process steps may be interchanged in any order without departing from the scope of the invention as long as such an interchange does not contradict the claim language and is not logically nonsensical.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for determining glucose concentration in the blood of a user, the method comprising the steps of:
   collecting psychometric data for the user;
   using a light source to bleach retinal pigments in the eye of the user;
   after bleaching the retinal pigments, presenting a visual perceptual task on a display device to the user, the visual perception task based on the psychometric data;
   sensing neurophysiological brain activity of the user while presenting the visual perception task on the display device; and
   in a processor, correlating the sensed neurophysiological brain activity to the glucose concentration in the blood of the user.

2. The method of claim 1, wherein the step of presenting a visual perceptual task comprises displaying, on the display device, a sequence of images to the user, the sequence of images including a specific target.

3. The method of claim 2, further comprising displaying, on the display device, a plurality of sequences of images that each include the specific target.

4. The method of claim 3, wherein:
   the step of sensing neurophysiological brain activity of the user comprises sensing event-related potentials (ERPs); and
   the method further comprises, in the processor:
      measuring amplitude and latency of peaks in the neurophysiological brain activity while the plurality of sequences of images are displayed; and
      correlating changes in the amplitude and latency to visual pigment regeneration rate.

5. The method of claim 1, wherein the step of presenting a visual perceptual task comprises displaying, on the display device, an image to the user, the image oscillating at a predetermined frequency.

6. The method of claim 5, wherein:
   the step of sensing neurophysiological brain activity of the user comprises sensing steady state visual evoked response potentials (SSVEPs); and
   the method further comprises, in the processor:
      determining changes in amplitude of the SSVEPs at the predetermined frequency; and
      correlating changes in the amplitude to visual pigment regeneration rate.

7. The method of claim 1, further comprising:
   establishing baseline neurophysiological brain activity for the user;
   sensing one or more environmental parameters; and
   using the baseline neurophysiological brain activity and the one or more sensed environmental parameters to correlate the sensed neurophysiological brain activity to the glucose concentration in the blood of the user.

8. The method of claim 1, further comprising:
   generating an alert to remind the user to check blood glucose concentration.

9. The method of claim 1, further comprising:
   generating feedback representative of the glucose concentration in the blood of the user.

10. A method for determining glucose concentration in the blood of a user, the method comprising the steps of:
    using a light source, bleaching retinal pigments in the eye of the user to cause the eye to undergo retinal pigment regeneration;
    displaying a plurality of sequences of images on a display device to the user, each sequence of images including a specific target; and
    in a processor, measuring amplitude and latency of peaks in event-related potentials while the plurality of sequences of images are displayed;
    correlating changes in the amplitude and latency to visual pigment regeneration rate; and correlating the visual pigment regeneration rate to the glucose concentration in the blood of the user.

11. A non-invasive blood glucose concentration sensing system, comprising:
- a neurophysiological brain activity sensor configured to sense event-related potentials (ERPs) of a user and supply signals representative thereof;
- a display device responsive to display commands to render images;
- a light source coupled to the processor and configured to selectively emit a bleaching light into an eye of the user to bleach retinal pigments in the eye; and
- a processor coupled to the display device and the neurophysiological brain activity sensor and configured to:
  - control emission of the bleaching light from the light source,
  - after emission of the bleaching light from the light source, present a visual perceptual task to the user by commanding the display device to render a sequence of images to the user, the sequence of images including a specific target,
  - command the display device to render a plurality of sequences of images that each include the specific target,
  - measure amplitude and latency of peaks in the neurophysiological brain activity while the plurality of sequences of images are displayed,
  - correlate changes in the amplitude and latency to visual pigment regeneration rate, and
  - correlate the visual pigment regeneration rate to blood glucose concentration of the user.

12. The system of claim 11, wherein the processor is further configured to generate an alert to remind the user to check blood glucose concentration.

13. The system of claim 11, wherein the processor is further configured to generate feedback representative of the glucose concentration in the blood of the user.

14. A method for determining glucose concentration in the blood of a user, the method comprising the steps of:
- using a light source, bleaching retinal pigments in the eye of the user to cause the eye to undergo retinal pigment regeneration;
- displaying an image to the user on a display device, the image oscillating at a predetermined frequency;
- sensing steady state visual evoked response potentials (SSVEPs) while the image is being displayed; and
- in a processor, determining changes in amplitude of the SSVEPs at the predetermined frequency;
- correlating changes in the amplitude to visual pigment regeneration rate; and
- correlating the visual pigment regeneration rate to the glucose concentration in the blood of the user.

15. A non-invasive blood glucose concentration sensing system, comprising:
- a neurophysiological brain activity sensor configured to sense steady state visual evoked response potentials (SSVEPs) of a user and supply signals representative thereof;
- a display device responsive to display commands to render images;
- a light source coupled to the processor and configured to selectively emit a bleaching light into an eye of the user to bleach retinal pigments in the eye; and
- a processor coupled to the display device and the neurophysiological brain activity sensor and configured to:
  - control emission of the bleaching light from the light source,
  - after emission of the bleaching light from the light source, present a visual perceptual task to the user by commanding the display device to render an image oscillating at a predetermined frequency,
  - determine changes in amplitude of the SSVEPs at the predetermined frequency,
  - correlate changes in the amplitude to visual pigment regeneration rate, and
  - correlate the visual pigment regeneration rate to blood glucose concentration of the user.

16. The system of claim 15, wherein the processor is further configured to generate an alert to remind the user to check blood glucose concentration.

17. The system of claim 15, wherein the processor is further configured to generate feedback representative of the glucose concentration in the blood of the user.

* * * * *